US006406754B2

(12) United States Patent
Chappa et al.

(10) Patent No.: US 6,406,754 B2
(45) Date of Patent: Jun. 18, 2002

(54) COATING PROCESS AND APPARATUS

(75) Inventors: Ralph A. Chappa, Prior Lake; Steven J. Porter, Minnetonka, both of MN (US)

(73) Assignee: SurModics, Inc., Eden Prairie, MN (US)

( * ) Notice: Subject to any disclaimer, the term of this patent is extended or adjusted under 35 U.S.C. 154(b) by 0 days.

(21) Appl. No.: 09/847,030

(22) Filed: May 1, 2001

Related U.S. Application Data

(62) Division of application No. 09/456,925, filed on Dec. 8, 1999, now Pat. No. 6,254,921.

(51) Int. Cl.[7] .......................... A61L 27/00; A61F 2/02; A61F 2/06

(52) U.S. Cl. .................. 427/385.5; 623/1.44; 427/2.24

(58) Field of Search ................................ 427/2.3, 2.24, 427/2.28, 430.1, 256, 261, 286; 118/404, 405, 423, DIG. 18, DIG. 19; 623/1.1, 1.44

(56) References Cited

U.S. PATENT DOCUMENTS 5,501,734 A * 3/1996 Oliphant ..................... 118/234
5,531,715 A * 7/1996 Engelson et al. ........... 604/265
6,106,889 A * 8/2000 Beavers et al. .............. 427/2.1

OTHER PUBLICATIONS

LaPorte, Richard J., "Coating Application and Curing Techniques", Chapter 6 of *Hydrophilic Polymer Coatings for Mecial Devices*, Technomic Publishing Co., Inc., pp. 113–129.

* cited by examiner

*Primary Examiner*—Bret Chen
*Assistant Examiner*—Jennifer Kolb Michener
(74) *Attorney, Agent, or Firm*—Merchant & Gould P.C.

(57) ABSTRACT

A process and apparatus for dip-coating intermediate and/or discrete discontinuous portions of longitudinal devices, including medical devices such as catheters and guidewires. The apparatus provides a chamber in which both the desired portion(s) of the device and the coating solution can be controllably contacted. A controlled coating can be achieved within the chamber by providing and controlling one or more of the following relationships: a) the manner in which a chamber (containing solution) is itself moved with respect to a static device, b) the manner in which the device is moved with respect to a fixed chamber position containing a fixed volume of solution, and/or c) the manner in which both the chamber and device are fixed in position, and the coating is achieved by adding and removing a volume of solution from the chamber. The resultant movement of solution and device is intended to mimic or replicate the relative movements involved in a conventional dip-coating procedure, at least along the length of device to be coated.

9 Claims, 9 Drawing Sheets

COATING PROCESS AND APPARATUS

This application is a divisional of U.S. application Ser. No. 09/456,925, filed Dec. 8, 1999,now U.S. Pat. 6,254,921.

TECHNICAL FIELD

In one aspect, the present invention relates to coating processes, such as dip coating processes, for coating the surfaces of long, cylindrical or tubular materials. In particular, the invention relates to dip coating processes and apparatuses for coating the external surfaces of medical materials such as catheters and guidewires.

BACKGROUND ART

Many medical devices, particularly those implanted in the body on either a permanent, temporary or transient bases, are often provided with surface coatings intended to achieve a particular purpose, such as improved lubricity, biocompatibily, hemostasis, or the like.

Conventional applications of such dip coating techniques are described, for instance, in U.S. Pat. Nos. 5,429,618; 5,443,453; 5,464,650; 5,541,167; 5,531,715; 5,538,512; 5,603,991 and 5,702,823, the disclosures of each of which are incorporated herein by reference.

Dip coating has long been used as a common coating technique, and its applicability to medical devices is well established. See, for instance, "Coating Application and Curing Techniques", Chapter 6 in Hydrophilic Polymer Coatings for Medical Devices, Catheters, R. J. LaPorte, ed. (1997), which describes the advantages associated with this method as including lower equipment costs, and complete, uniform, application of the coating to the device. Disadvantages, however, may include the need for relatively large volumes of coating fluid.

The above advantages are most apparent, however, in situations where either the entire device (such as a catheter or guidewire), or even a discrete terminal portion thereof, is to be coated. In such cases, it is quite easy to dip the entire device, or the distal portion, into the necessary solution(s). A further, and particular, disadvantage of dip coating techniques, however, arises in the situation where it is necessary to coat only intermediate and/or discontinuous portions of the device. Often, for instance, both distal ends of a device are not to be coated (e.g., in the event they provide a different structural feature or function than the intermediate portion(s)).

Intermediate and discontinuous coatings are typically provided in one of two ways—either by somehow masking the areas not to be coated, in order to prevent them from contacting the coating solution, or by simply not permitting coatings in certain areas to become effectively bound thereto (e.g., shielding them from the application of curing radiation, and the like).

Such approaches, however, are themselves cumbersome, and can be particularly wasteful of coating reagents. Typically, for instance, the entire masking material, once coated with the coating material, will simply be discarded if not reused. Clearly new and improved methods and apparatuses for coating intermediate would provide a variety of advantages.

SUMMARY OF THE INVENTION

Figure 1:
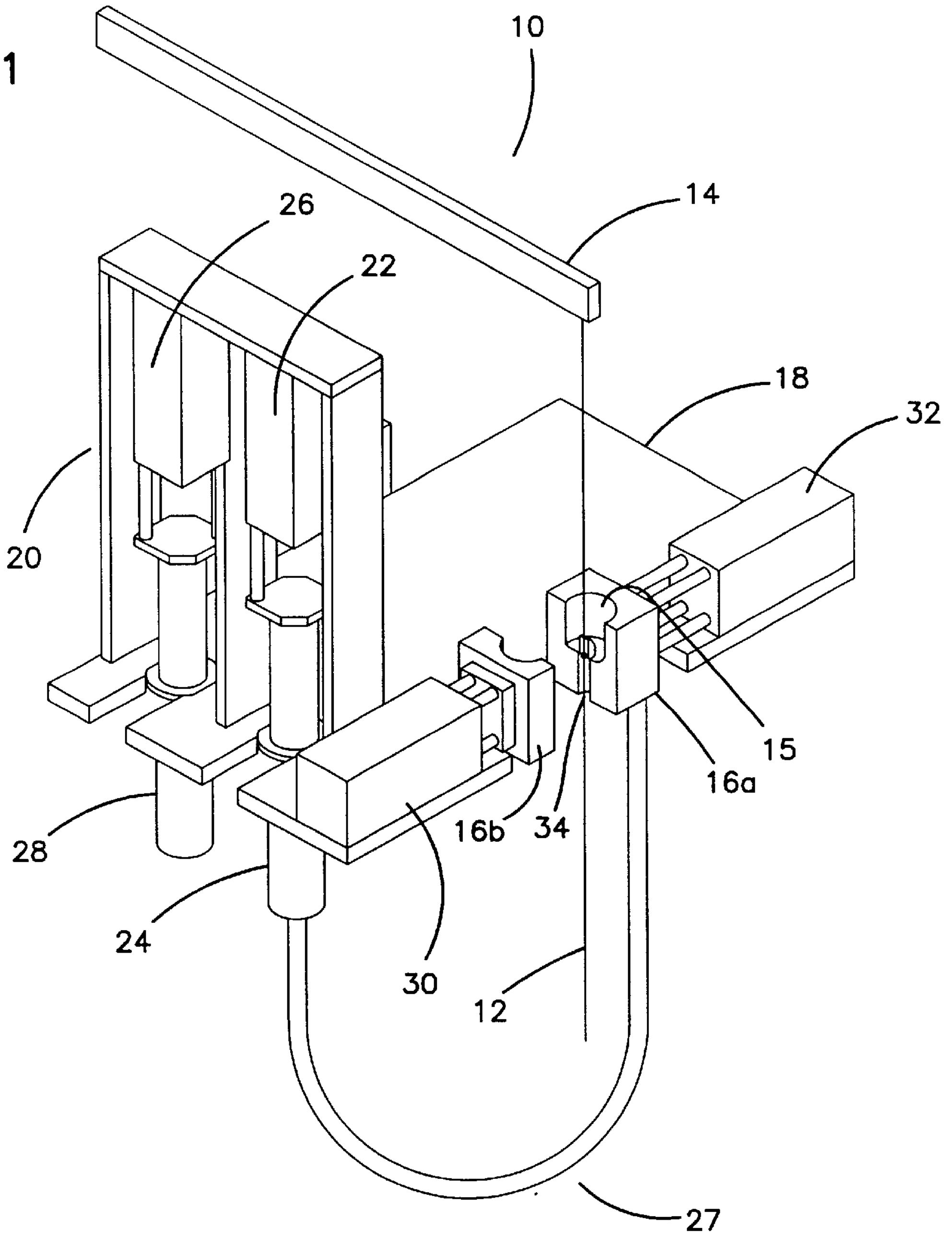
FIGS. 1–3 show sequential steps in the use of a preferred embodiment of an apparatus of this invention.

The present invention provides a process and apparatus for dip coating intermediate and/or discrete discontinuous portions of medical devices, and preferably those devices provided in a tubular, wire-like or generally cylindrical configuration, such as catheters and guidewires. The invention provides an optimal combination of such properties as cost savings, coating efficiency, flexibility, reproducibility, and ease of use. The process and apparatus of this invention, in turn, are particularly well suited to incorporation into automated coating processes.

In essence, a preferred apparatus provides a chamber in which both the desired portion(s) of the device and the coating solution can be controllably contacted. In turn, portions of the device that are not to be coated remain outside the chamber, and effectively out of contact with the solution, during the coating process. The resultant movement of solution and device is intended to mimic or replicate the relative movements involved in a conventional dip coating procedure, at least along the length of device to be coated. As a result, the apparatus provides significant benefits, as well as an improved intermediate or periodic coatings.

In a preferred embodiment, the process for coating a longitudinal device, e.g., a tubular or wire-like medical device, using an apparatus as described herein comprises the following steps, in any suitable order:

a) providing a chamber adapted to sealably and removably retain part or all of the intermediate portion to be coated along the length of a longitudinal device, and adapted to contain a volume of coating solution sufficient to coat the retained intermediate portion, b) sealably positioning some or all of the intermediate portion of the longitudinal device in the chamber and providing a volume of coating solution in the coating chamber, c) contacting the solution with the intermediate portion, within the chamber, and thereafter removing the solution from contact with the intermediate portion, in a manner sufficient to permit a coating to be retained on the intermediate portion, and d) removing the coated intermediate portion from its sealed relationship within the chamber.

Optionally, and preferably, the process can include whatever preceding or subsequent steps may be desired in order to provide the desired coating, e.g., surface preparation steps, coating cure steps, and/or the application of multiple coating layers. Any or all of these steps can be incorporated at any suitable point in the process of this invention, including with the intermediate portion still in position within the chamber.

An apparatus of this invention, in turn, provides: a) a chamber adapted to sealably and removably retain an intermediate portion of a longitudinal device, and adapted to contain a volume of coating solution sufficient to coat the retained intermediate portion, b) a fluid delivery/recovery system adapted to deliver and/or recover a quantity of coating solution to and/or within the chamber in a predetermined manner, and c) a system for moving an intermediate and/or periodic portions of a longitudinal device into and out of a sealed relationship within the chamber. The word "intermediate", as used herein, will generally refer to a portion that is between, but not including, the ultimate distal and proximal ends of a longitudinal device. The word "periodic", as used herein, will generally refer to a plurality of such intermediate portions, of the same or varying lengths or types, along a single device.

The invention further provides a longitudinal device having an overall length substantially greater than its maximum diameter, such as a catheter or guidewire, having an intermediate and/or periodic portions coated using the apparatus and process of this invention.

An apparatus of this invention can also be incorporated as a station in a multistation work line for fabricating or processing a device, such that much or all of the entire process can be automated and controlled in a cost effective manner. In turn, the invention further provides a multistation work line for fabricating longitudinal devices, such as medical devices, the work line comprising an apparatus as described herein in functional combination with one or more other stations (e.g., a surface preparation (e.g., primer application, wash) station, surface analysis station, and/or a curing station such as a radiation or light curing assembly or a thermal oven).

In a particularly preferred embodiment, the present invention is used to coat the intermediate and/or periodic portions of longitudinal medical devices with coating solutions containing reagents having photoreactive groups. Once coated using the present method and apparatus, the resulting uncured coating (including the reagents themselves and/or other chemical moieties present therein) can be covalently attached to the device surface by the activation of those photoreactive groups (e.g., by the application of UV energy).

DETAILED DESCRIPTION

The present invention provides a process and apparatus for coating intermediate and/or discontinuous portions of medical devices, and preferably those longitudinal devices provided in a tubular or generally cylindrical configuration, such as catheters and guidewires.

In essence, a preferred apparatus provides a chamber in which both the desired portions of the device and the coating solution can be controllably contacted. In turn, portions of the device that are not to be coated remain outside the chamber, and/or otherwise out of contact with the solution, during the coating process. The process can be used to coat one or more intermediate, discrete portion of any desired length, as well as periodic intermediate portions having either the same or different lengths, and either the same or different uncoated spacing portions between them. In yet another embodiment, a plurality of portions along a device can be coated with a respective plurality of different coating solutions, e.g., solutions containing different concentrations of the same or similar composition, or containing compositions that are different in whole or in part. The apparatus can be adapted for use with any device amenable to coating in a dip coating process, and is particularly useful for those devices having portions along their length that are to remain uncoated or differently coated.

A controlled coating can be achieved within the chamber by providing and controlling one or more of the following relationships, including combinations and permutations thereof: a) the manner in which a chamber (containing solution) is itself moved with respect to a static device, b) the manner in which the device itself is moved with respect to a fixed chamber position containing a fixed volume of solution, and/or c) the manner in which both the chamber and device are fixed in position, and the coating is achieved by adding and removing a volume of solution from the chamber.

Figure 2:
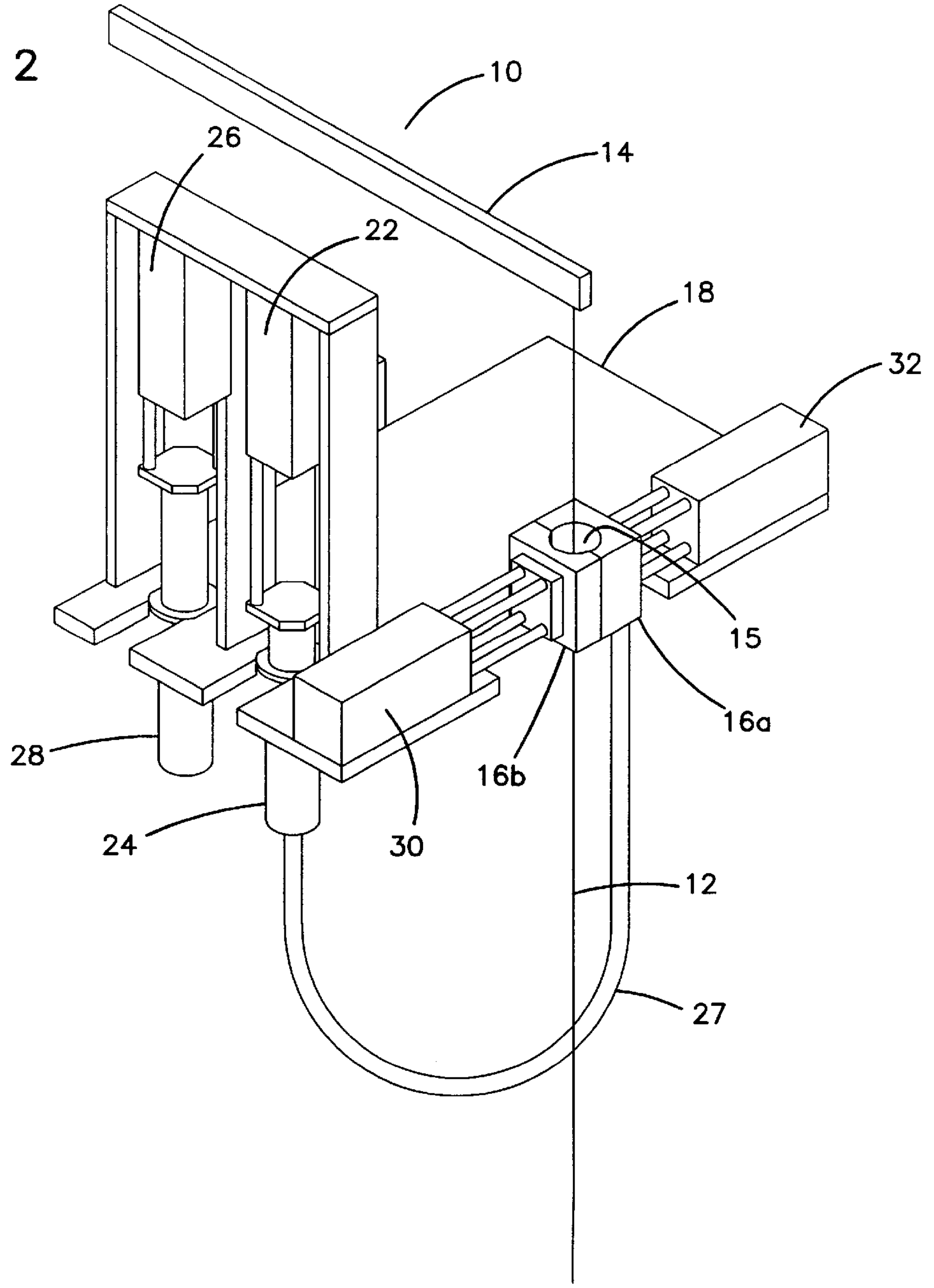
Figure 3:
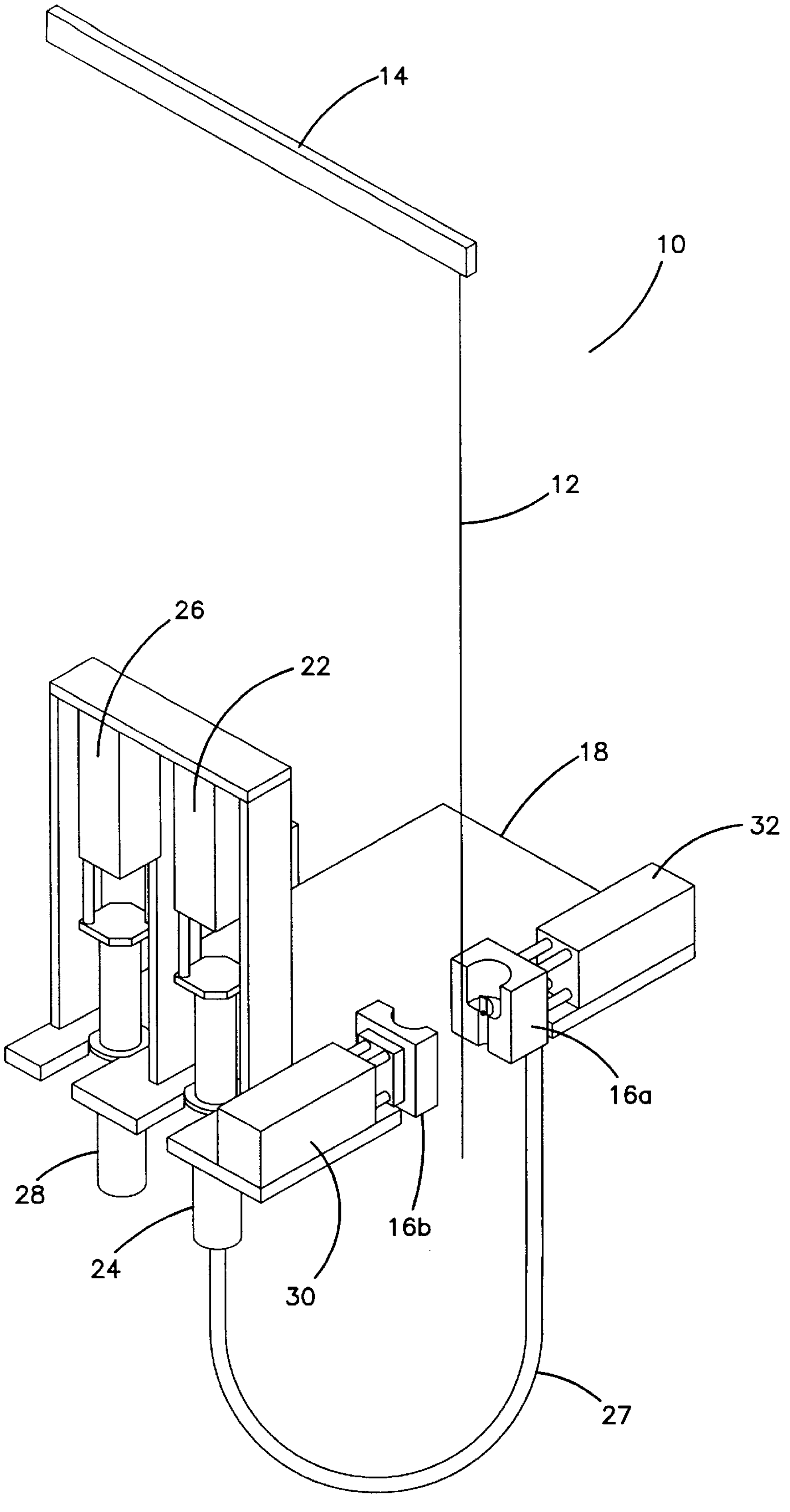

The embodiment shown and described with respect to FIGS. 1–3 herein, incorporates aspects of both embodiments a) and c) above, in that it provides a chamber that can be moved longitudinally (e.g., downward) with respect to a static device, thereby coating a corresponding portion of the device. This movement can be followed by the removal of solution from the chamber in a manner that coats the remaining portion, corresponding to the height of the coating solution, thus also incorporating aspects of embodiment c) above. Clearly the embodiment of FIGS. 1–3 could incorporate aspects of embodiment b) above, were the device itself to be moved in its longitudinal direction. The embodiment shown and described with respect to FIGS. 4–9, by contrast, largely incorporates embodiment c) above, in that both the chamber and devices can remain static and in place during the actual "dip coating" step, with the coating achieved solely by the delivery and recovery of solution therefrom.

An apparatus of this invention, in turn, provides a chamber adapted to sealably and removably retain an intermediate portion of a tubular device, and adapted to contain a volume of coating solution sufficient to coat most, if not substantially all, of the retained intermediate portion. Preferably, the dimensions and shape of the chamber are sufficient to permit the device to be retained therein without contacting any interior portions (e.g., interior walls) of the chamber, with the exception of whatever inlet and/or exit apertures may be used to seal the chamber around the device. The inlet and exit apertures, in turn, are adapted to be sealed around the device in a manner that prevents leakage of the coating solution, while not damaging the device itself. In a preferred embodiment, the chamber can be configured to have offset portions and an effectively funnel-shaped interior base (as described below), to permit the solution and/or the device to be separated from contact in a controlled manner that facilitates a uniform coating.

The apparatus further provides a fluid delivery/recovery system adapted to deliver and/or recover a quantity of coating solution to the chamber in a predetermined manner. The fluid delivery/recovery system can be either manual (e.g., syringes), automated (e.g., computer controlled pneumatically driven syringes), semi-automated, or any combination thereof.

Finally, the apparatus provides a system for moving an intermediate and/or periodic portions of a tubular device into and out of a sealed relationship within the chamber. In preferred embodiments, for instance, a device moving system includes a holder adapted to hold one or more distal portions of one or more devices in a fixed desired orientation during the coating procedure. The holder can be used to hold one or more devices in a fixed position and in a manner that permits the chamber itself to be removably formed around the device itself, an embodiment of which is shown in FIGS. 1–3. The holder can also be adapted to hold one or more devices in a fixed position removed from the chamber (or components used to form a chamber), in order to permit the entire device/holder assembly to then be positioned within a chamber, an embodiment of which is shown in FIGS. 4–9 herein.

The invention will be further described with reference to the Drawing, in which FIGS. 1–3 show sequential steps in the use of a preferred apparatus 10. As shown, and described with respect to the coating of a wire 12, the wire is positioned and retained in a generally vertical fashion using upper holding fixture 14. Optionally, and preferably, a lower holding fixture (not shown) is used as well, in order to provide the wire with a desire tension and stable orientation.

A generally cup-shaped chamber 15 is formed around a desired portion of the wire by bringing together two half cup portions, 16*a* and 16*b* , respectively. A platform plate 18 is attached to an electro-mechanical actuator (not shown) that is adapted to retain and move the chamber up and/or down with respect to the catheter/wire holding fixture (and in turn, with respect to the catheter or wire itself) which, in the embodiment shown, remains stationary with respect to the fixture. A pneumatic fluid delivery/recovery system 20 is employed to fill and drain the chamber. The system includes syringes 24 and 28 for both the delivery and recovery of coating solution, as well as respective pneumatic syringe actuators 22 and 26, respectively.

The syringe assemblies can be used separately or in tandem. In the embodiment presently shown, for instance, only syringe 24 is shown as being used to fill chamber 15 via fluid hose 27. The syringe can therefore be used to both deliver and withdraw solution to and from the chamber. In an alternative embodiment (not shown), a system of check valves and tubing adapters (e.g., Y-adapters) can be employed to permit the cooperative use of both syringe assemblies, e.g., permitting one to deliver and the other to withdraw during a single filling/emptying cycle. Using a system of check valves and appropriate connectors, and given the present description, those skilled in the appropriate art can provide any suitable flow path diagram, e.g., one that permits the incorporation of a fluid reservoir into the system, and its use in maintaining desired fluid levels in both the first and second syringes.

In use, as shown in FIG. 2, at the appropriate time, left chamber cup portion 16*b* has extended forward in order to contact right chamber cup portion 16*a*, with the wire suitably positioned between the two, thereby effectively sealing an initial wire portion to be coated between them. A pneumatic system is used to both open and close the cup portions forming the chamber, as shown by pneumatic cylinders 30 and 32, respectively. As shown, the chamber can be open to the atmosphere on its upper end, while its lower end (shown as orifice 34 enclosing a portion of the wire) is sufficiently sealed (e.g., with a rubber, plastic or sponge-like material) to prevent coating solution from leaking. Once the chamber has been formed and positioned around the wire, pneumatic air cylinder 22 is extended, pushing syringe 24 downward. Fluid (coating solution) from syringe 24, in turn, is pumped into the chamber in order to fill the chamber, thus making contact with the intermediate portion of the wire positioned therein. With the solution in contact with the wire, the platform plate 18 can itself be moved, preferably in a downward direction, and in a controllable and predetermined fashion, until a desired length of the wire has been coated.

Once the desired portion has been coated, the solution is withdrawn from the chamber by operation of the syringe assembly. With the base of the chamber slanted toward a single position along its wall, and the exit port positioned at substantially the lowest point of the slanted base, and adjacent the wall, the base effectively funnels the solution away from the wire portion as it drains. This movement prevents puddling of the solution near the wire as the solution drains, and provides a final, relative movement between the wire and solution that further enhances the coating efficiency and quality.

An apparatus as shown in FIGS. 1–3 has particular use in coating long or discontinuous portions of the device, since either the device itself and/or chamber can be moved with respect to each other. A potential disadvantage of this approach, however, arises with longitudinal devices that vary considerably in diameter along their length and/or that have fragile regions. With such devices it can be difficult to move the chamber along the length thereof, without taking special precautions (e.g., in the design of the aperture or gasket that serves to seal the chamber around the device).

An alternative preferred embodiment is shown in sequential FIGS. 4–9. As compared to the previous embodiment, in which the coating solution is exemplified as moving along a static wire or other device by the movement of the chamber containing the solution, the present embodiment provides an apparatus in which both the devices and chamber remain static during the actual coating process, and the desired movement of the coating solution with respect to the devices is achieved by the process of filling and emptying the chamber.

As shown in this embodiment, an apparatus 40 is provided in which one or more wires or catheters 48 are retained on a device holding assembly 42, which proceeds along a path into an area between matching chamber-forming plates 54 and 56, respectively. Once positioned within the chamber formed by the joining of those plates, a pump 58 is used to controllably deliver and remove coating solution into the chamber, thus coating the wires/catheters. Once the coating solution has been removed from the chamber, the plates are again separated, permitting the coated wires to proceed further along the work station and into curing station 62. The overall process and components of one preferred apparatus will be described in greater detail below.

Figure 4:
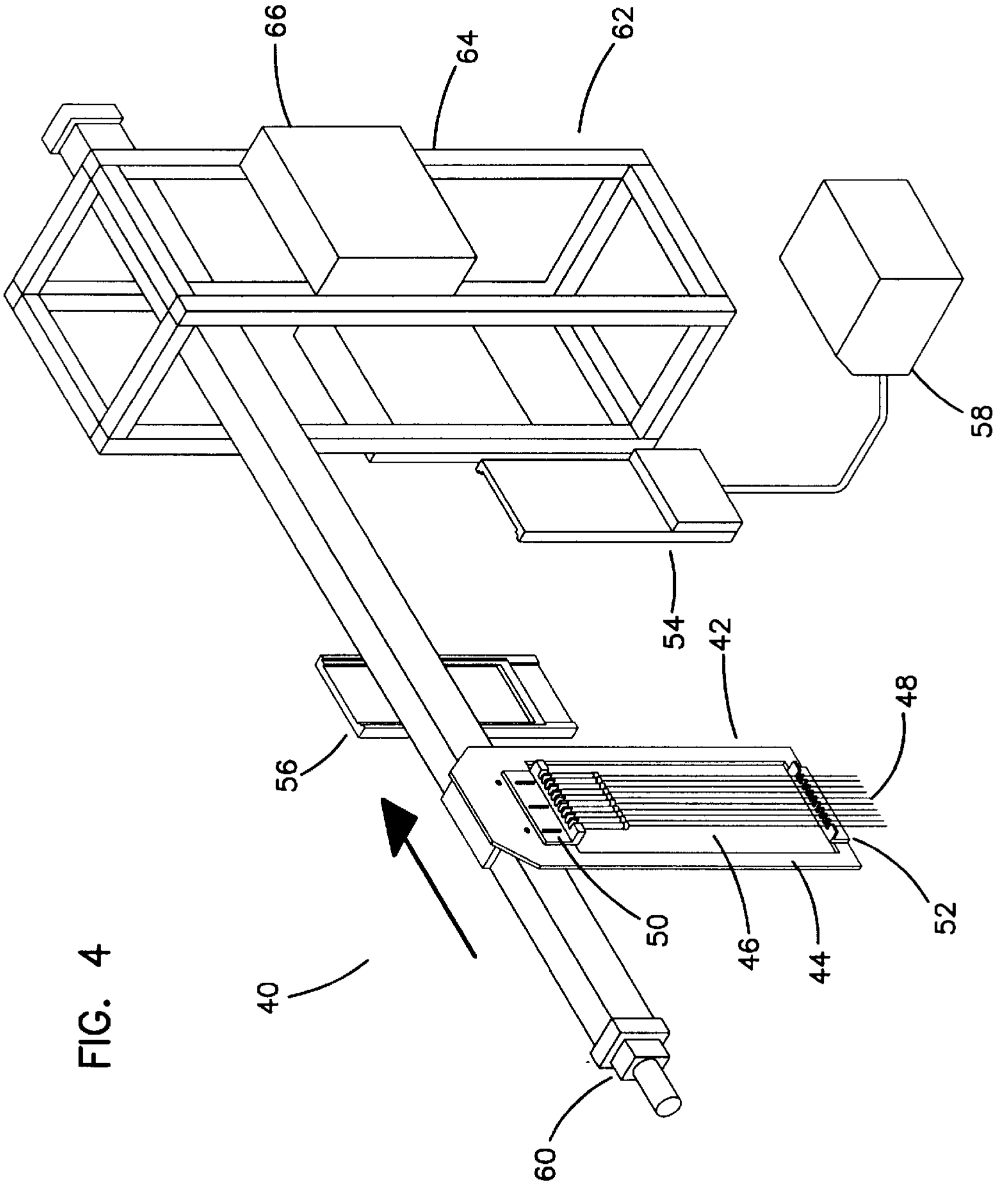
FIGS. 4–9 show sequential steps in the use of an alternative preferred embodiment of the present invention.

As can be seen in FIG. 4, for instance, the catheters 48 are loaded onto the device holding assembly 42 by attaching them to an upper bracket 50 and lower bracket 52, each of which are fixedly attached to a framelike structure 44. The framelike structure provides an open area 46 of sufficient dimensions to permit UV radiation to be later delivered from both sides of the holding assembly. In essence, this embodiment includes the use of a device holding assembly 42, adapted to hold one or more devices and to them move along a path into position between matching reservoir plates. With the holding assembly and devices in position, the reservoir plates 54 and 56 are joined to form a chamber of sufficient dimensions to contain the device holder assembly 42, including the devices held thereon. A pump 58 is then used to both fill and drain the chamber in a predetermined manner (e.g., volume, speed). Those skilled in the art can appreciate the manner in which coatings of different types (e.g., thicknesses) can be achieved by controlling such parameters as the viscosity of the coating solution and the speed with which the devices and solution are moved with respect to each other within the chamber. Once drained, the chamber is again disassembled by separating the reservoir plates, and the device holding proceeds to a curing station, where IV lamps are used to expose the devices from one or more directions in order to cure the coating thereon. As such, in the particular embodiment shown, the length or dimensions of the portion to be coated is substantially limited to the dimensions of the catheter holding assembly, and in turn, the chamber formed during the operation.

Figure 5:
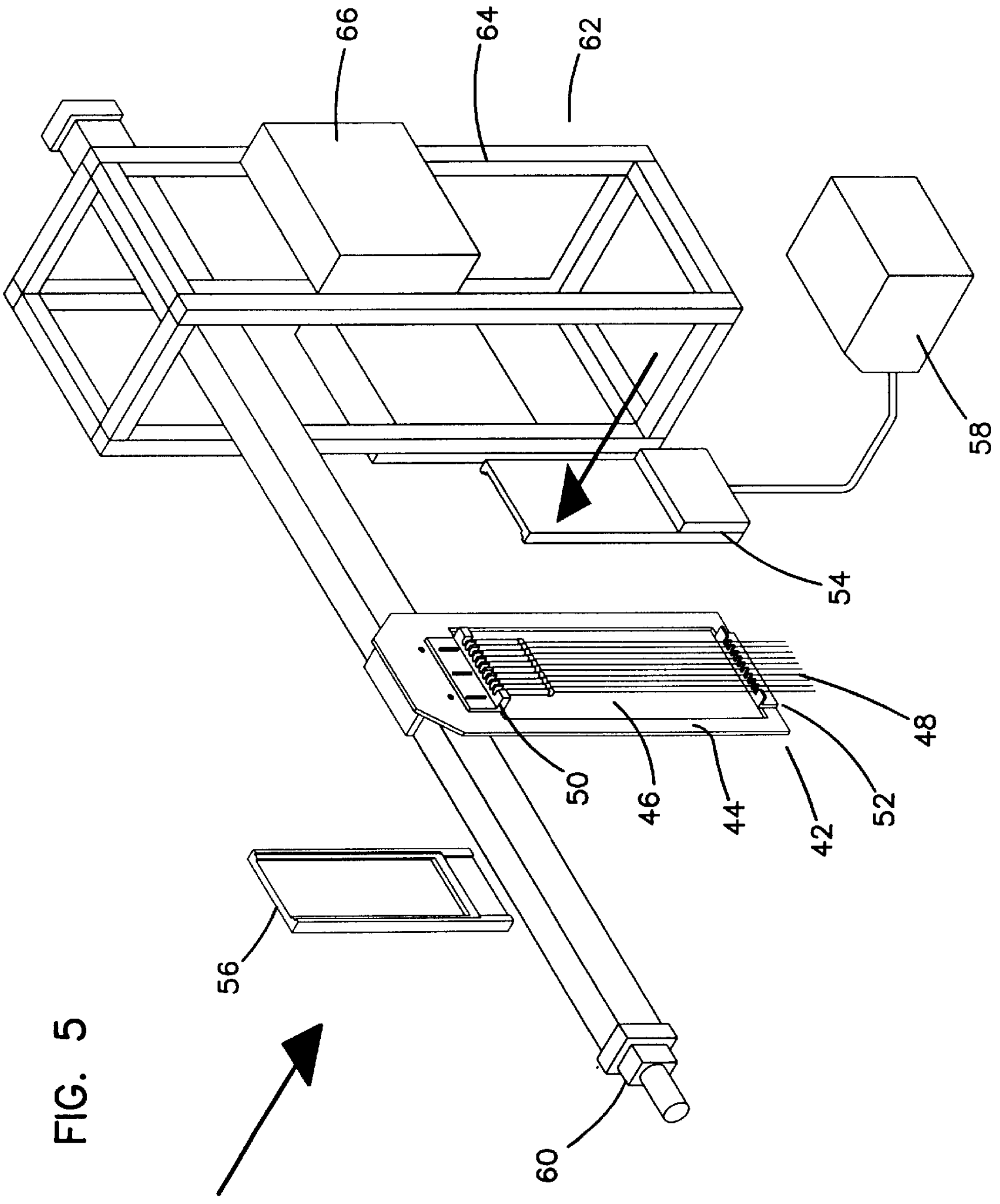

In FIG. 5, the entire device holding assembly 42, including devices held thereon, are moved by the screw drive actuator 60 along the work path, stopping between reservoir plates 54 and 56. These matching plates are moved forward into sealed contact with each other, and with the catheter assembly within, by the use of pneumatics or an electromechanical device (not shown). Once contacted, a gasket on one or both plates forms a chamber seal around the plates and catheters.

Figure 6:
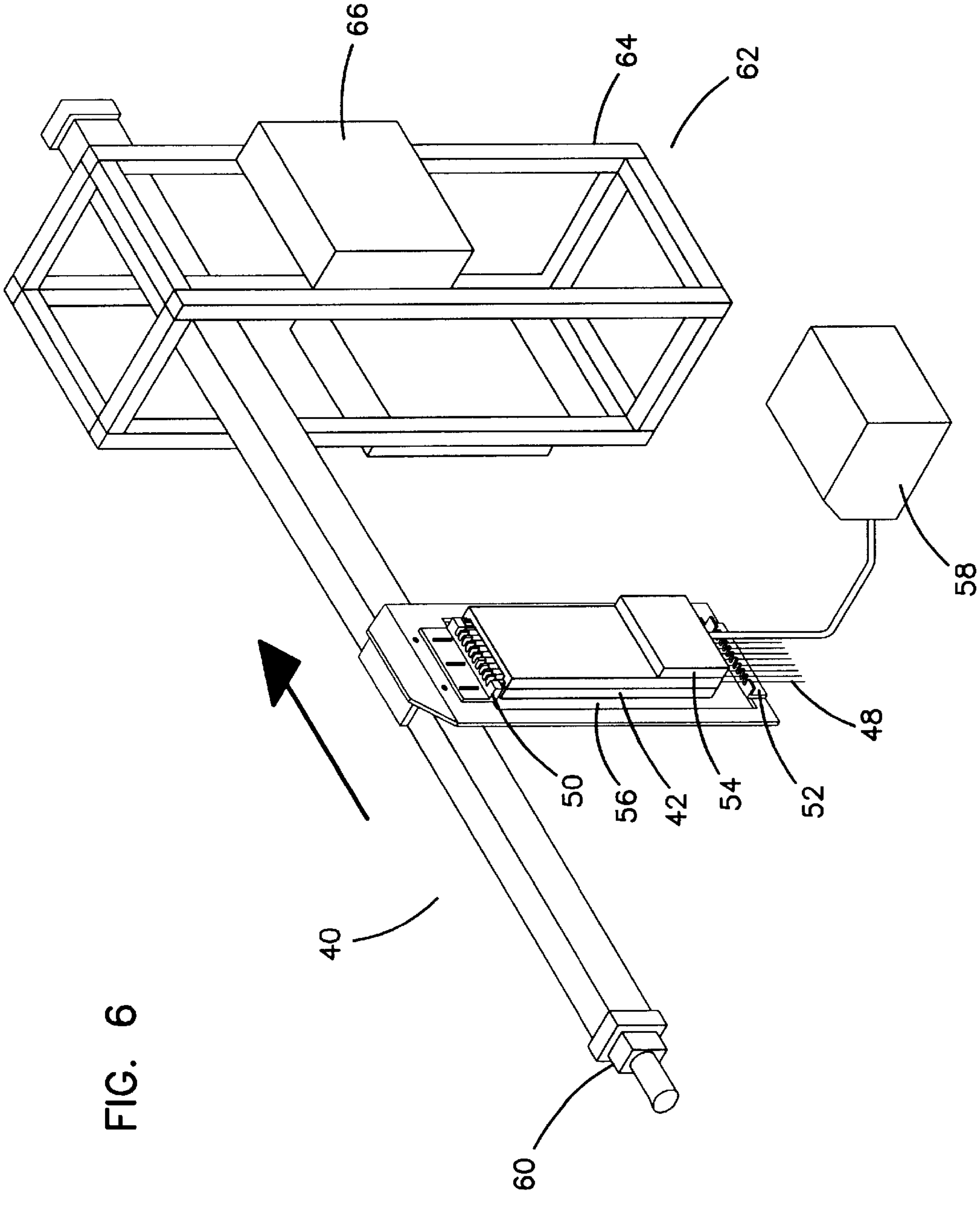

As shown in FIG. 6, coating solution is pumped into the chamber via a fluid conduit attached to plate 54, using a peristaltic pump 58, causing the fluid to flow upward between the plates until the desired coating length is reached. Once the fluid reaches a predetermined height it is permitted to dwell in contact with the catheter portions for a desired period of time. After the dwell time, fluid is pumped out from between the plates using the peristaltic pump.

Figure 7:
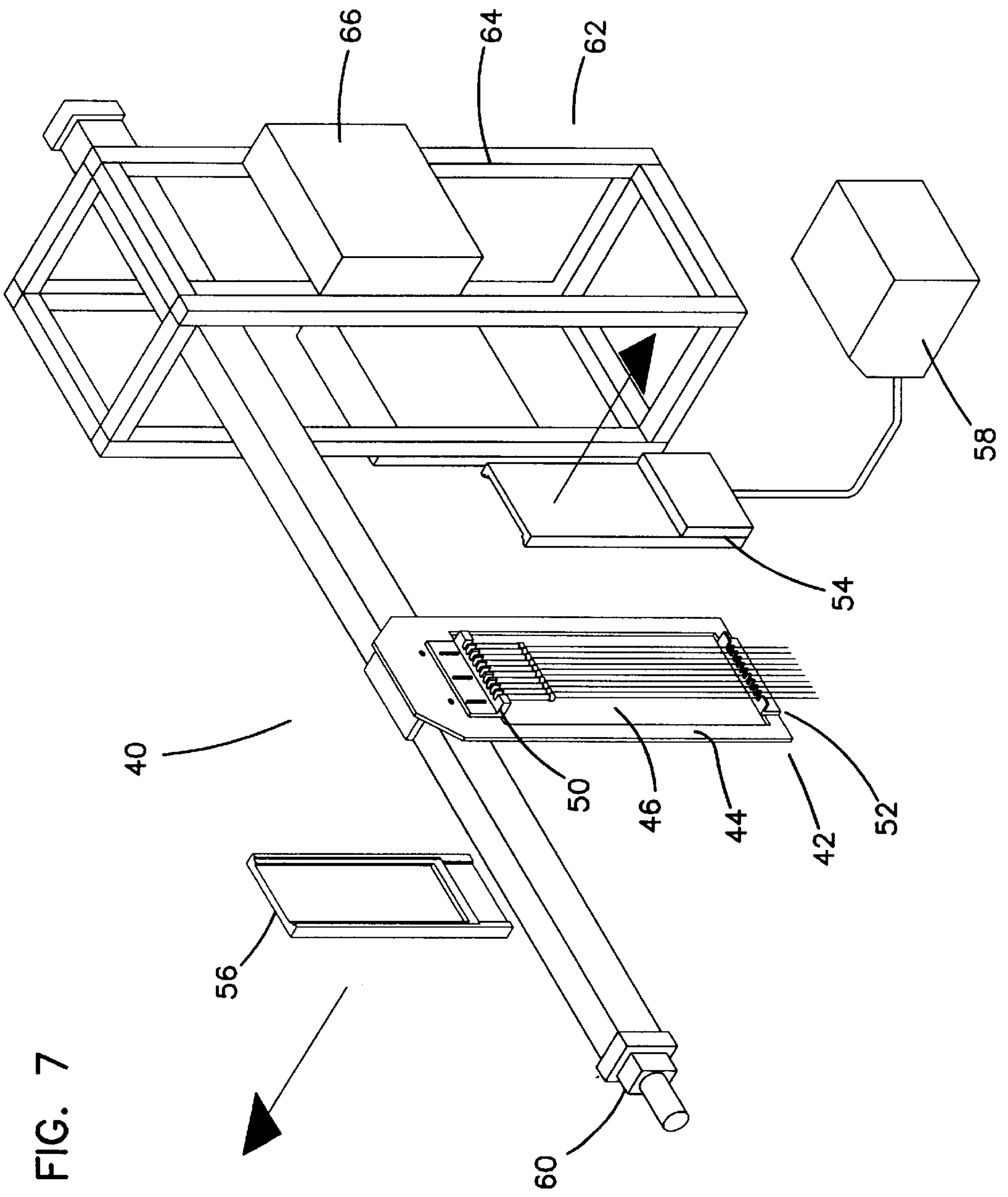
Figure 8:
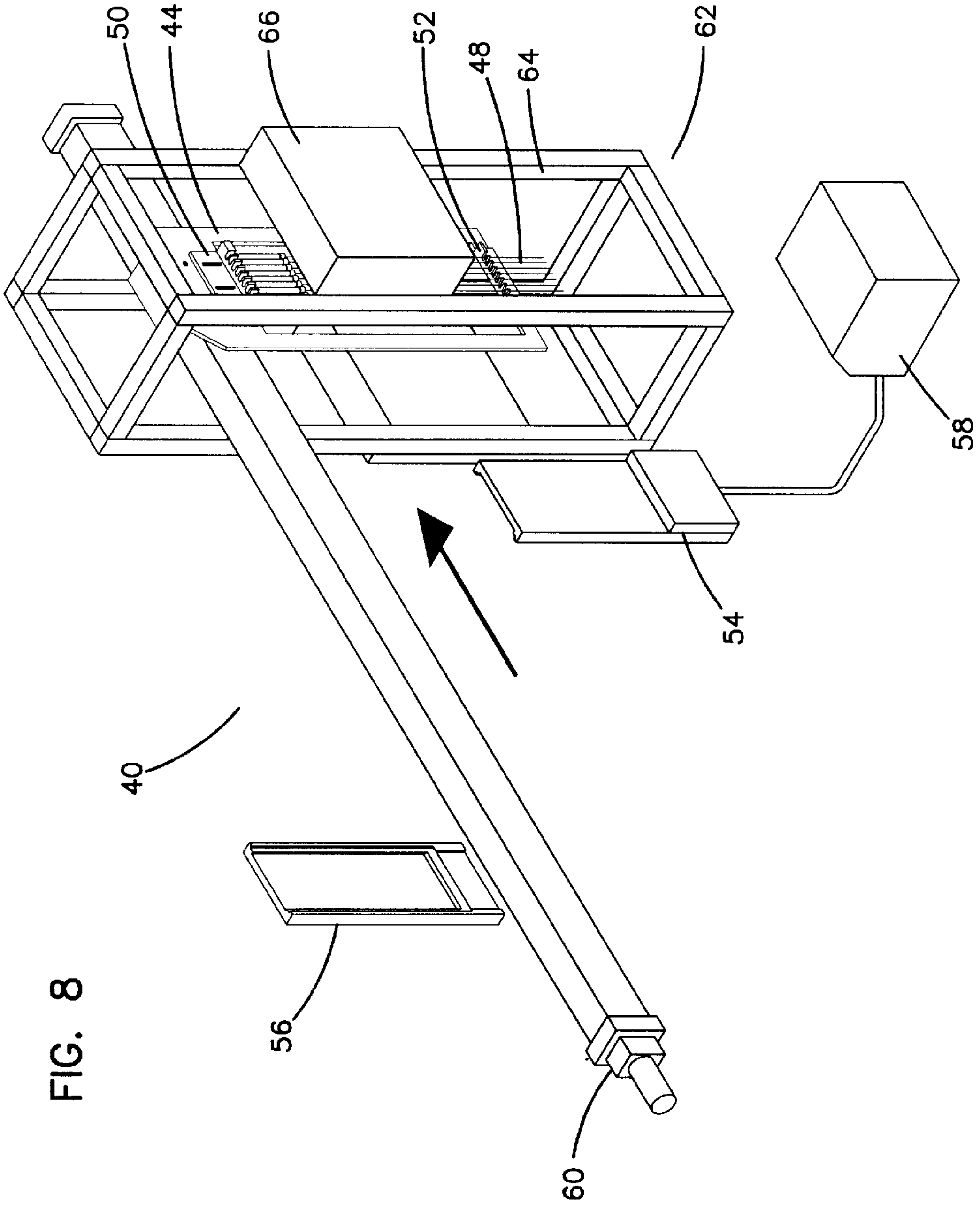
Figure 9:
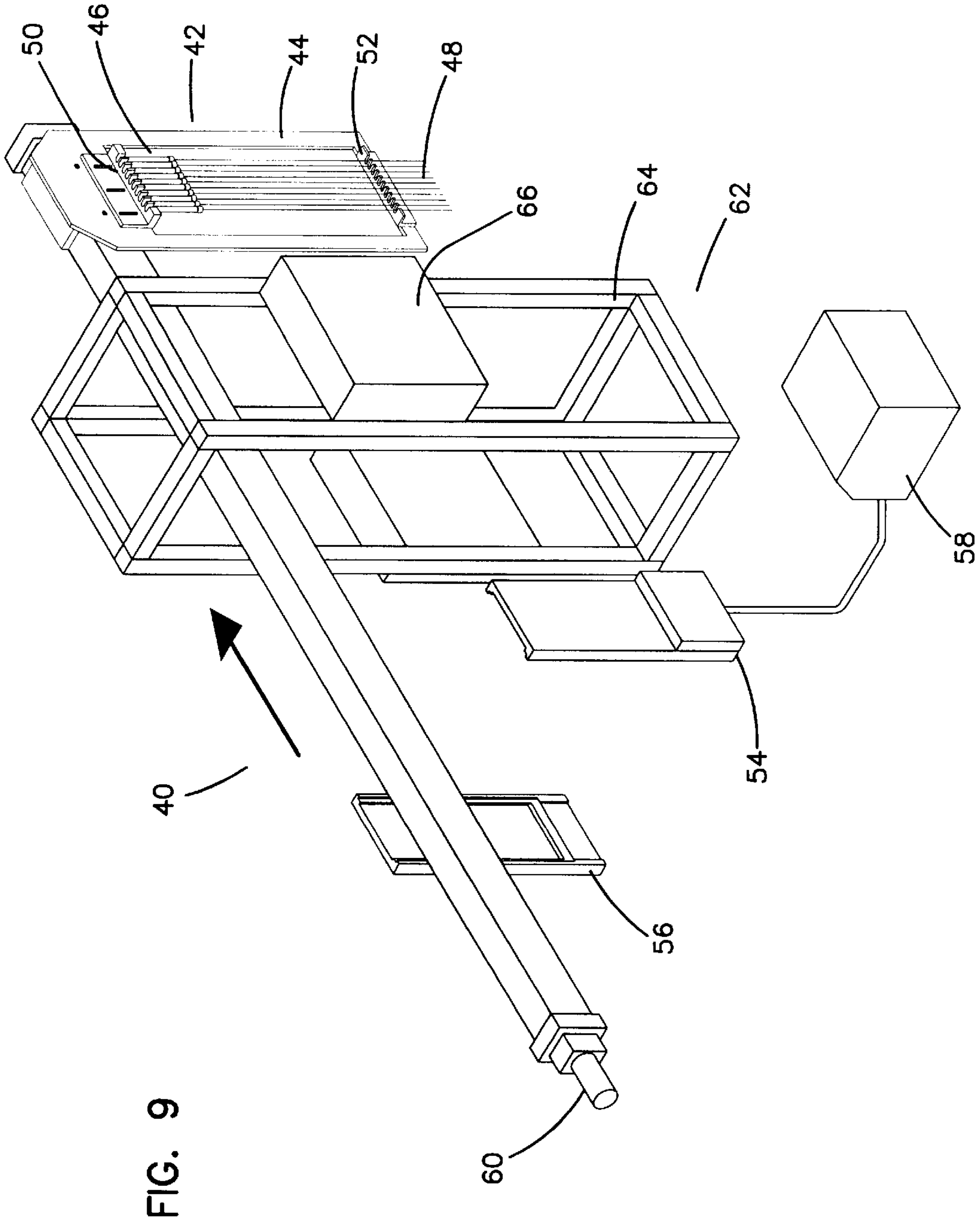

Moving to FIG. 7, it can be seen that plates 54 and 56 are separated, breaking the seal between them and disassembling the chamber formed therein, causing the gasket on each plate to release, allowing the device holder assembly 42and the parts attached to move to the curing station 62). In FIG. 8, the catheter holding assembly is moved by the screw drive actuator further along the path, and into position within the lamp housing 64. The curing process, including the types, orientation and distances of the lamps 66 themselves, as well as the curing time, can be adapted for any particular application using techniques available to those in the art. Finally, and as seen in FIG. 9, the catheter assembly, including the catheters with the cured coating thereon, are removed from the curing station and either unloaded or moved on for further processing.

An apparatus as shown in FIGS. 4–9 has particular advantages as well, in that it is particularly well suited for handling multiple devices simultaneously, as well as devices having fragile portions or unusual geometries. This apparatus is less preferred, however, in the coating of lengths longer than the height of the chamber itself, unless accommodations are made to again move either the device and/or the chamber in opposite directions with respect to each other.

In a particularly preferred embodiment, the present invention is used to coat the intermediate and/or periodic portions of longitudinal medical devices with coating solutions containing reagents having photoreactive groups. Once coated using the present method and apparatus, the resulting uncured coating (including the reagents therein) can be covalently attached to the device surface by the activation of those photoreactive groups (e.g., by the application of UV energy). Suitable reagents are described, for instance, in various patents assigned to the assignee of the present invention, including U.S. Pat. Nos. 4,722,906; 4,973,493; 4,979,959; 5,002,582; and 5,512,329, the disclosures of each of which are incorporated herein by reference. Such reagents can be used in the process and with the apparatus of this invention to provide and coat coating solutions having viscosities between about 0.2 centipoise (cp) to about 500 cp, and preferably between about 1 cp and about 250 cp.

The invention further provides a longitudinal medical device having an intermediate and/or periodic portions coated using the apparatus and process of this invention. A preferred medical device is generally in the form of a catheter or guidewire. Examples of suitable medical devices include, for instance, angioplasty balloon catheters (e.g., where no coating is desired on the balloon itself); guidewires (e.g., where no coating is desired on the proximal end, to accommodate handling and/or on the distal end, to accommodate positioning); electrophysiological catheters (e.g., where no coating is desired on the electrode portion thereof); and emboli collection catheters (where no coating is desired on the emboli collection basket).

The present invention has been described with respect to various preferred embodiments. It is understood that the claims herein are not to be limited by the particular embodiments described.

We claim:

1. A longitudinal device selected from the group consisting of catheters and guidewires having one or more intermediate or period portions thereof coated using a process for coating intermediate and discrete discontinuous portions of the longitudinal device, said device free of a coating at the distal tip, the process comprising the steps of:

a) providing a chamber adapted to sealably and removably retain part or all of the intermediate portion to be coated along the length of a longitudinal device, and adapted to contain a volume of coating solution sufficient to coat the retained intermediate portion, b) sealably positioning some or all of the intermediate portion of the longitudinal device in the chamber and providing a volume of coating solution in the coating chamber, c) contacting the solution with the intermediate portion, within the chamber, and thereafter removing the solution from contact with the intermediate portion, in a manner sufficient to permit a coating to be retained on the intermediate portion, and d) removing the coated intermediate portion from its sealed relationship within the chamber.

2. A device according to claim 1 wherein the process is used to coat a single intermediate, discrete portion along the length of the device.

3. A device according to claim 1 wherein the process is used to coat periodic intermediate portions having either the same of different lengths, and either the same or different uncoated spacing portions between them.

4. A device according to claim 1 wherein the process is used to coat one or more intermediate portions along the device with a respective plurality of different coating solutions.

5. A device according to claim 1 wherein the process is adapted to provide a coating by controlling: a) the manner in which a chamber, containing solution, is itself moved with respect to a static device, b) the manner in which the device is moved with respect to a fixed chamber position containing a fixed volume of solution, and/or c) the manner in which both the chamber and device are fixed in position, and the coating is achieved by adding and removing a volume of solution from the chamber.

6. A device according to claim 5 wherein the process incorporates aspects of both embodiments a) and c) above, by providing a chamber that can be moved downward with respect to a static device, thereby coating at least a portion of the device, which is followed by the removal of solution form the chamber in a manner that coats the remaining portion.

7. A device according to claim 5 wherein the process of embodiment c) above, that both the chamber and device(s) remain static during the coating process, with the coating achieved solely by the delivery and recovery of solution to and from the chamber.

8. A device according to claim 1 wherein the coating solution comprises a photoreactive reagent and the process comprises the further step of curing the coated reagent on the device by the application of radiant energy.

9. A device according to claim 1 wherein the device comprises a catheter selected from the group consisting of angioplasty balloon catheters, electrophysiological catheters, and emboli collection catheters.

* * * * *